(12) United States Patent
Biedermann et al.

(10) Patent No.: US 9,072,545 B2
(45) Date of Patent: Jul. 7, 2015

(54) ROD-SHAPED IMPLANT, IN PARTICULAR FOR THE DYNAMIC STABILIZATION OF THE SPINE

(75) Inventors: Lutz Biedermann, VS-Villingen (DE); Wilfried Matthis, Weisweil (DE)

(73) Assignee: Biedermann Technologies GmbH & Co. KG, Donaueschingen (DE)

(*) Notice: Subject to any disclaimer, the term of this patent is extended or adjusted under 35 U.S.C. 154(b) by 1006 days.

(21) Appl. No.: 12/435,894

(22) Filed: May 5, 2009

(65) Prior Publication Data

US 2009/0281573 A1    Nov. 12, 2009

Related U.S. Application Data

(60) Provisional application No. 61/050,967, filed on May 6, 2008.

(30) Foreign Application Priority Data

May 6, 2008 (EP) .................................... 08008529

(51) Int. Cl.
*A61B 17/70* (2006.01)

(52) U.S. Cl.
CPC ......... *A61B 17/7029* (2013.01); *A61B 17/7019* (2013.01); *A61B 17/7028* (2013.01); *A61B 17/7031* (2013.01); *A61B 17/7032* (2013.01); *A61B 17/7037* (2013.01)

(58) Field of Classification Search
CPC ........... A61B 17/7019; A61B 17/7028; A61B 17/7029; A61B 17/7031; A61B 17/7032; A61B 17/7037

USPC .................................................. 606/254–259
See application file for complete search history.

(56) References Cited

U.S. PATENT DOCUMENTS

| 2004/0236328 | A1 | 11/2004 | Paul et al. |
| 2004/0267260 | A1 | 12/2004 | Mack et al. |
| 2005/0065515 | A1 | 3/2005 | Jahng |
| 2005/0124991 | A1 | 6/2005 | Jahng |
| 2005/0136764 | A1 | 6/2005 | Sherman et al. |
| 2006/0041259 | A1 | 2/2006 | Paul et al. |
| 2006/0129147 | A1 | 6/2006 | Biedermann et al. |
| 2006/0142758 | A1 | 6/2006 | Petit |
| 2006/0195093 | A1 | 8/2006 | Jahng |

(Continued)

FOREIGN PATENT DOCUMENTS

| DE | 10 2004 018 621 A1 | 11/2005 |
| WO | WO 2004/105577 A2 | 12/2004 |
| WO | WO 2006/071742 A2 | 7/2006 |

OTHER PUBLICATIONS

European Search Report for European Application No. 08008529.3 in the name of Biedermann Motech GmbH, European Search Report Dated Oct. 2, 2008 and mailed Oct. 13, 2008 (6 pgs.).

*Primary Examiner* — Jerry Cumberledge
*Assistant Examiner* — Nicholas Plionis
(74) *Attorney, Agent, or Firm* — Christie, Parker & Hale, LLP

(57) ABSTRACT

A rod-shaped implant for the dynamic stabilization of the spine includes at least a portion having a flexible first material forming a matrix in which a flexible structure having at least one fiber made of a second material is embedded. The rod-shaped implant can be compressed and extended along the longitudinal axis of the rod-shaped implant while it provides a high torsional stiffness.

20 Claims, 8 Drawing Sheets

(56) References Cited

U.S. PATENT DOCUMENTS

| | | |
|---|---|---|
| 2006/0229612 A1 | 10/2006 | Rothman et al. |
| 2007/0093820 A1 | 4/2007 | Freudiger |
| 2007/0129729 A1 | 6/2007 | Petit et al. |
| 2007/0161999 A1 | 7/2007 | Biedermann et al. |
| 2007/0233064 A1 | 10/2007 | Holt |
| 2007/0244481 A1 | 10/2007 | Timm |
| 2007/0270821 A1 | 11/2007 | Trieu et al. |
| 2007/0270843 A1 | 11/2007 | Matthis et al. |
| 2008/0065114 A1 | 3/2008 | Stone et al. |
| 2008/0183212 A1* | 7/2008 | Veldman et al. .............. 606/254 |
| 2008/0312694 A1 | 12/2008 | Peterman et al. |

\* cited by examiner

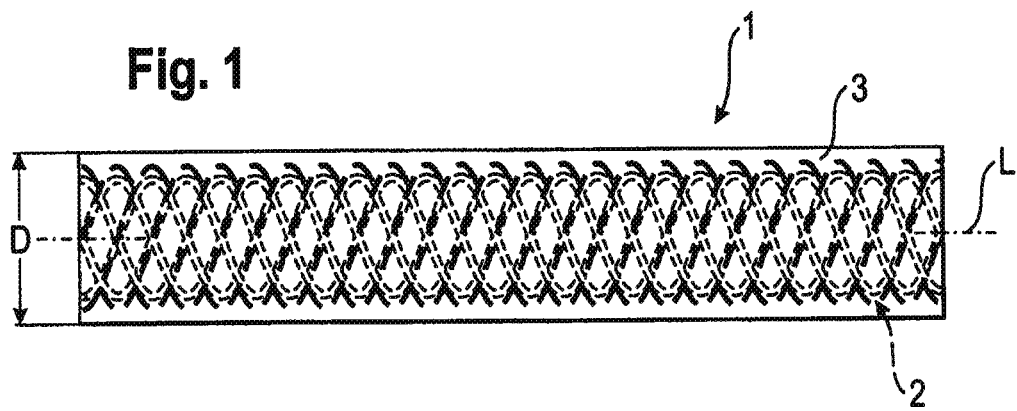
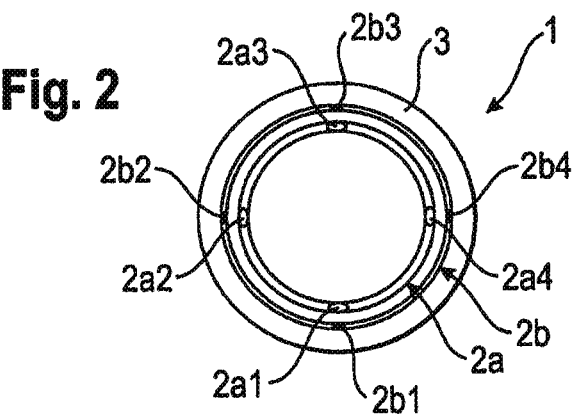
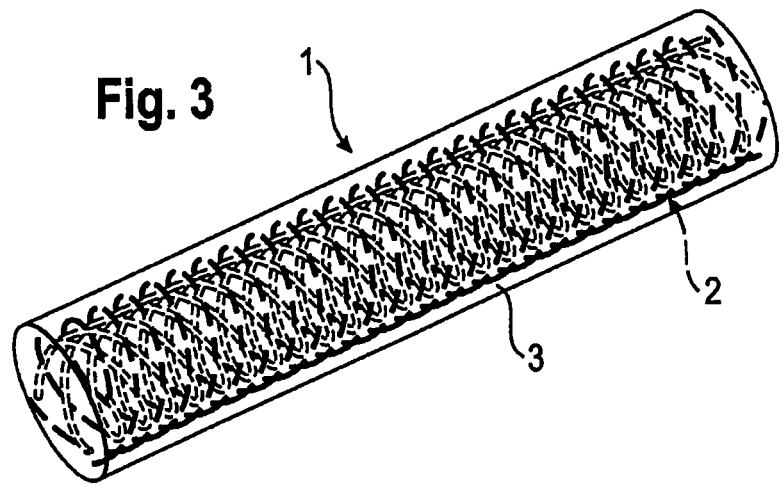

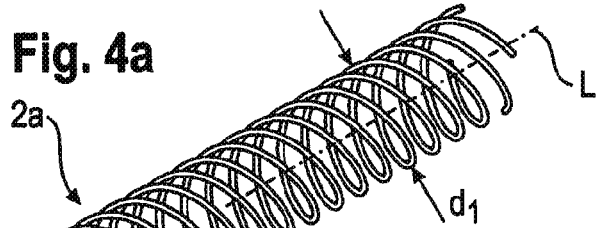
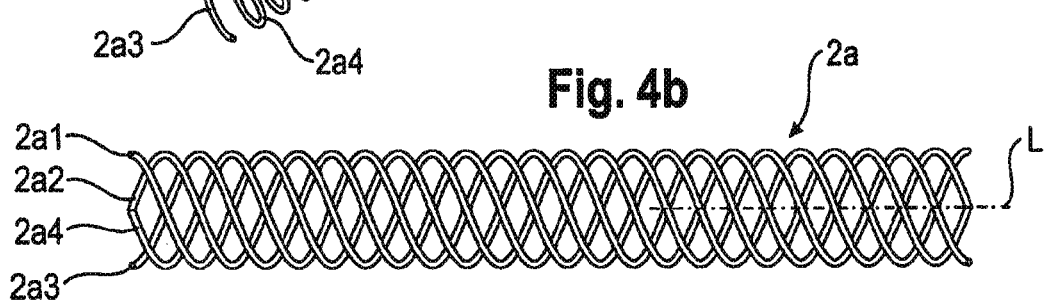
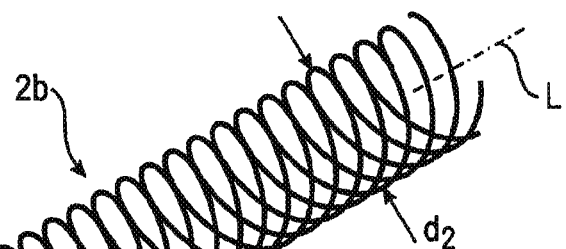
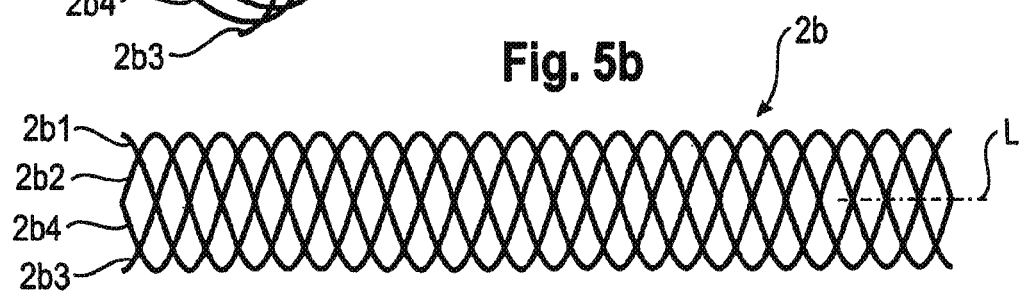

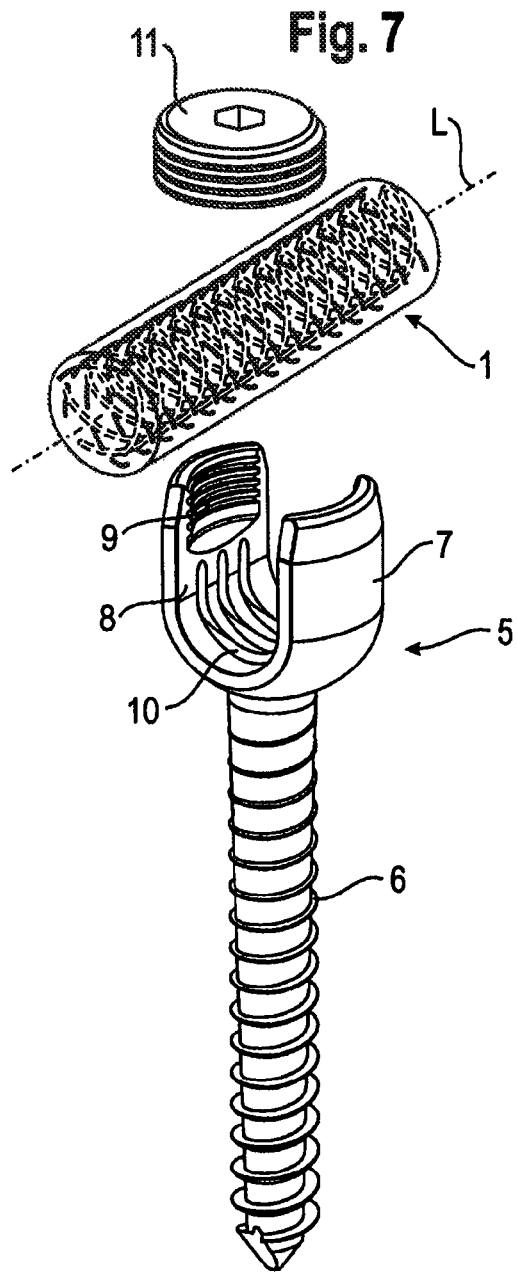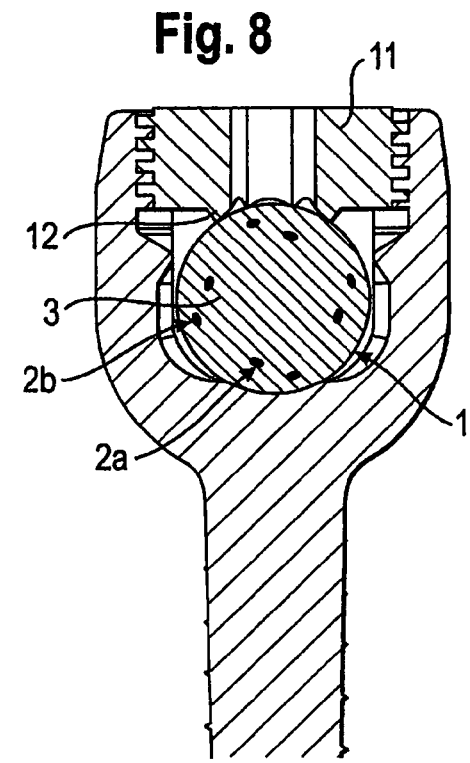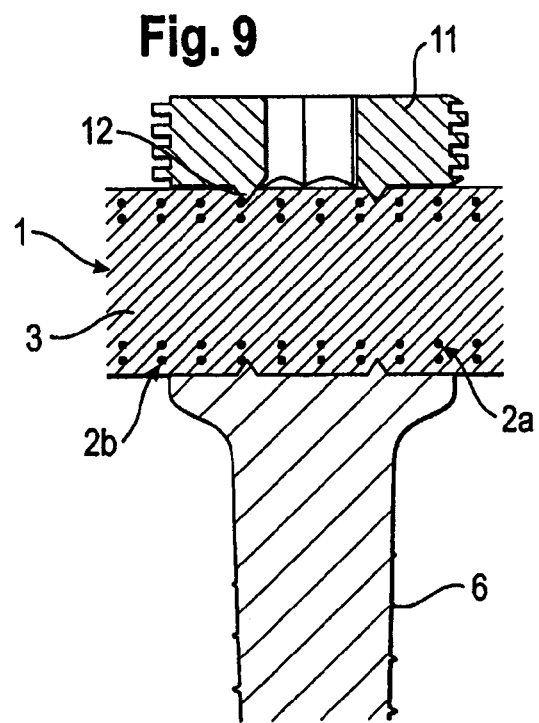

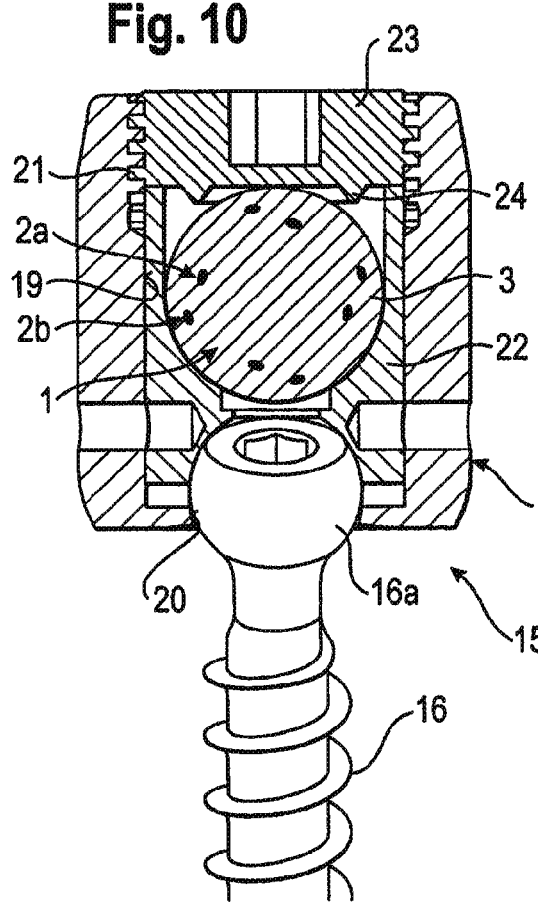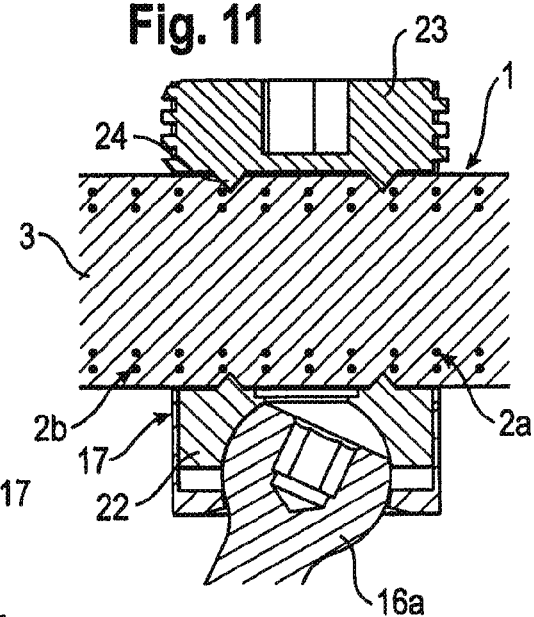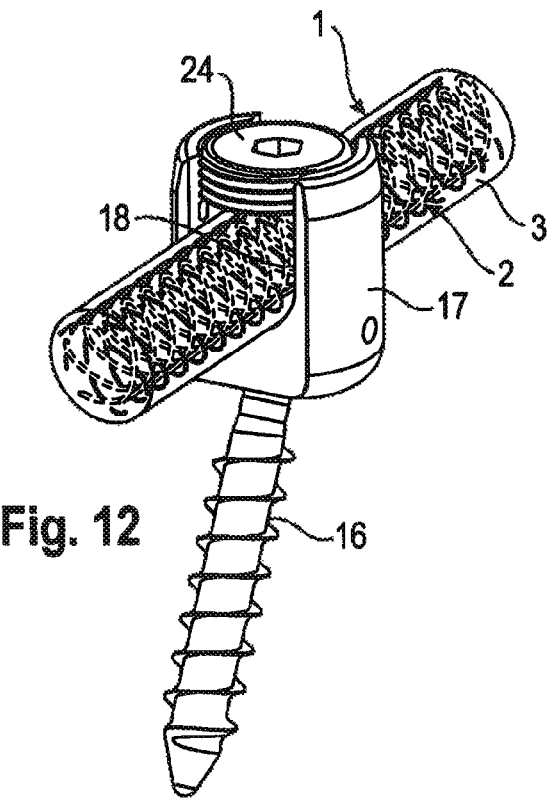

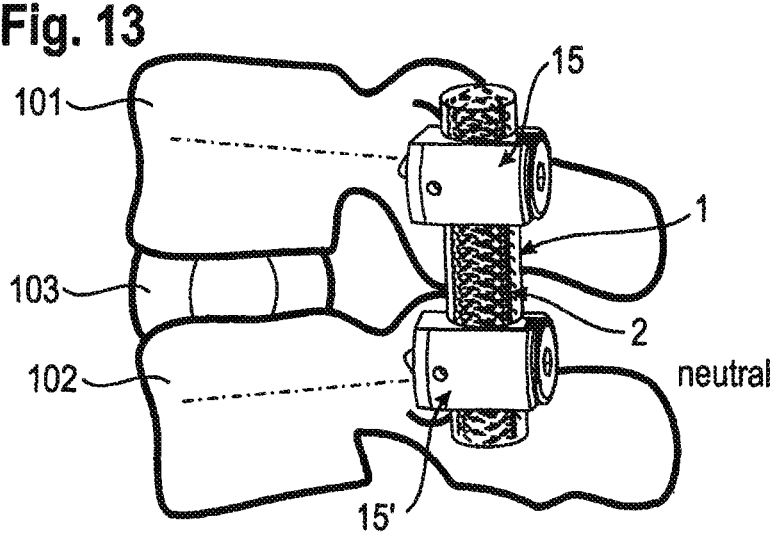
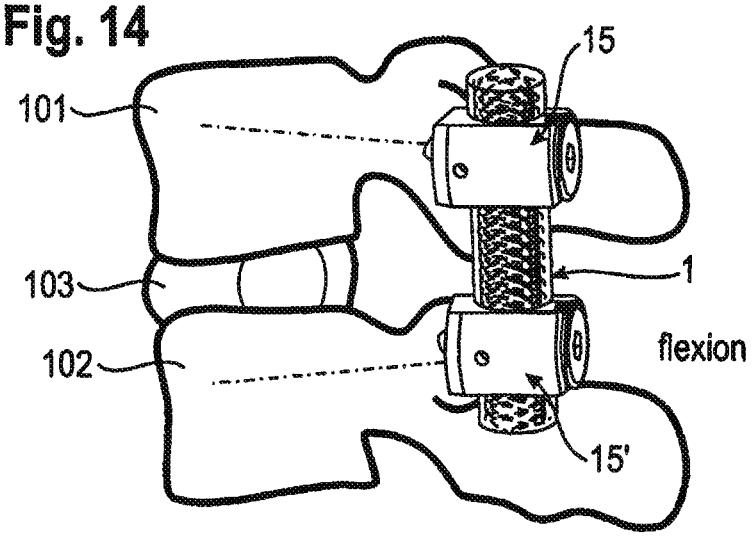
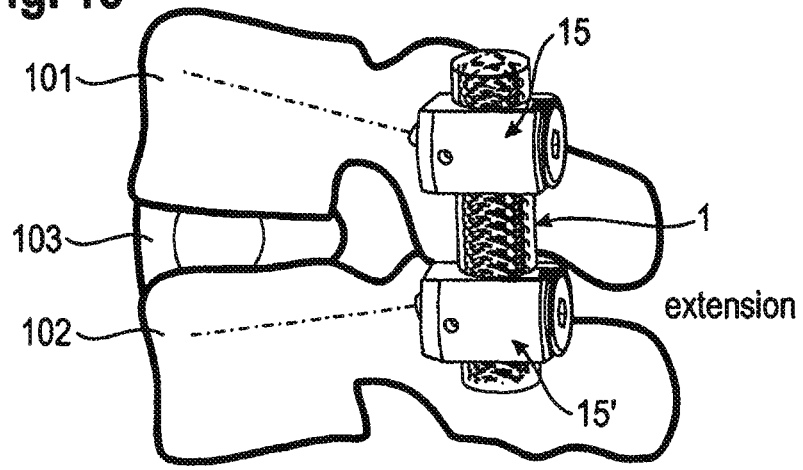

neutral compressed

ROD-SHAPED IMPLANT, IN PARTICULAR FOR THE DYNAMIC STABILIZATION OF THE SPINE

CROSS-REFERENCE TO RELATED APPLICATION(S)

The present application claims the benefit of U.S. Provisional Patent Application Ser. No. 61/050,967, filed May 6, 2008, the contents of which are hereby incorporated by reference in their entirety, and claims priority from European Patent Application EP 08 008 529.3, filed May 6, 2008, the contents of which are hereby incorporated by reference in their entirety.

BACKGROUND

The application relates to a rod-shaped implant, in particular for the dynamic stabilization of the spine.

A rod-shaped implant made of a plastic material for the dynamic stabilization of the spinal column is known, for example, from US 2007/0093820 A1, US 2007/0161999 A1 and US 2007/0270843 A1.

US 2006/0142758 A1 describes a linking element for a spinal fixing system which consists at least partly of a support made of polymeric material and a rod, bent or not, substantially coaxial with the support. The rod is, for example, made of a helical spring having an axis and coils which are at least partly embedded in the support made of polymer material. The helical spring is, for example, made of a metal or a metal alloy. The structure of the linking element permits compression and distraction in order to permit a dynamic stabilization of the spine.

SUMMARY

The disclosure provides a rod-shaped implant, in particular for the dynamic stabilization of the spine, which allows movements of the spinal motion segment stabilized by the implant in defined directions while preventing or suppressing movements in other directions.

The rod-shaped implant includes at least a portion which is made of a flexible first material forming a matrix in which a flexible structure comprising at least one fiber made of a second material is embedded.

The rod-shaped implant according to the disclosure has a flexibility which is dependent on the direction of the force acting between the vertebrae stabilized by the implant. It exhibits a particularly stiff behavior when a torsional force acts onto the rod while it allows an axial compression or extension when an axial compression or tension force acts onto the implant, respectively.

The flexible properties of the rod-shaped implant can be designed specifically according to the clinical requirements by selecting an appropriate flexible structure which is formed by fibers.

Further features and advantages of the invention will become apparent from the following detailed description of embodiments in conjunction with the accompanying drawings.

BRIEF DESCRIPTION OF THE DRAWINGS

FIG. 1 shows a schematic side view of a first embodiment of the rod-shaped implant.

FIG. 2 shows schematically a section of the implant according to FIG. 1 perpendicular to the rod axis.

FIG. 3 shows a schematic perspective view of the implant according to FIG. 1.

FIG. 4a shows a perspective view of a first example of an inner flexible structure of the rod-shaped implant of FIG. 1.

FIG. 4b shows a side view of the first inner flexible structure according to FIG. 4a.

FIG. 5a shows a perspective view of a first example of an outer flexible structure of the rod-shaped implant of FIG. 1.

FIG. 5b shows a side view of the outer flexible structure of FIG. 5a.

FIG. 6b shows a side view of the combined inner and outer flexible structure of FIG. 6a.

FIG. 7 shows an exploded view of the rod-shaped implant according to FIGS. 1 to 6b together with a monoaxial pedicle screw.

FIG. 8 shows a sectional view of the rod-shaped implant and the monoaxial screw according to FIG. 7 in the assembled state the section being taken perpendicular to the rod axis.

FIG. 9 shows a sectional view of the monoaxial screw with the rod-shaped implant of FIG. 7 in assembled state the section being taken along the rod axis.

FIG. 10 shows a sectional view of a polyaxial pedicle screw together with the rod-shaped implant according to FIGS. 1 to 6b in an assembled state the section being taken perpendicular to the rod axis.

FIG. 11 shows the polyaxial screw with the rod-shaped implant in section, the section being taken along the rod axis.

FIG. 12 shows a perspective view of the polyaxial screw of FIGS. 10 and 11 in an assembled state.

FIGS. 13 to 15 show the rod-shaped implant together with two pedicle screws fixed in adjacent vertebrae to stabilize the spinal motion segment in a neutral position of the vertebrae, in flexion and extension, respectively.

DETAILED DESCRIPTION

Figure 6A:
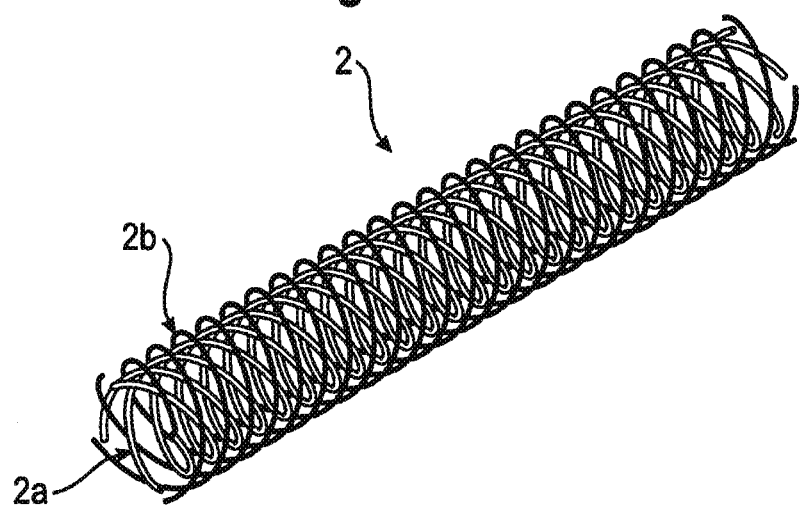
FIG. 6a shows a perspective view of the combined inner and outer flexible structure of FIGS. 4a to 5b.
Figure 6B:
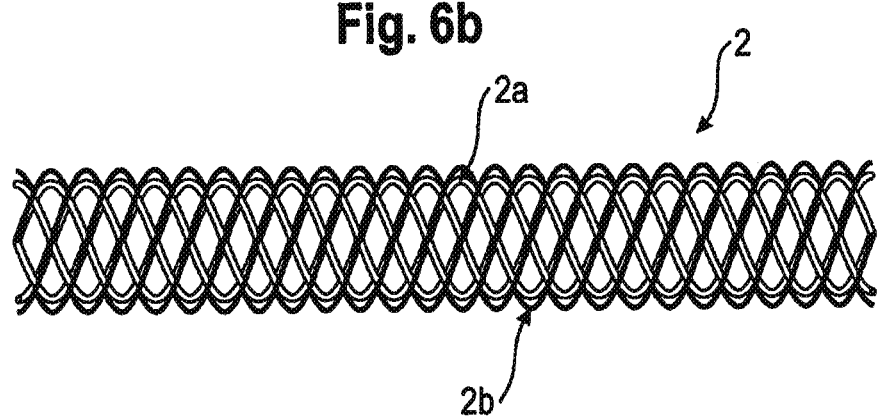

FIGS. 1 to 3 show the rod-shaped implant according to a first embodiment in a schematic side view, a cross sectional view and a perspective view. The rod-shaped implant 1 is substantially cylindrical in shape with an outer diameter D. The rod-shaped implant 1 includes a flexible structure 2 which is embedded into a matrix of polymeric material 3. The polymeric material exhibits flexibility and is preferably an elastomer. Examples for a suitable elastomer material are biocompatible polyurethanes or polycarbonate urethane (PCU). The outer diameter D of the rod-shaped implant can be designed such that the rod-shaped implant can be fixed in receiving parts of pedicle screws. The flexibility of the polymeric material is usually isotropic. In order to provide a direction-dependent specific flexibility to the rod-shaped implant, the flexible structure 2 is provided. As can be seen in particular from FIGS. 2 and 4a to 5b the flexible structure 2 according to the first embodiment comprises an inner structure 2a and an outer structure 2b. The inner structure 2a comprises four helices 2a1, 2a2, 2a3 and 2a4 which are arranged coaxially to the longitudinal axis L of the rod-shaped implant. The inner structure 2a has a first diameter $d_1$ which is the same for all four helices. The helices 2a1 to 2a4 are rotated with respect to each other by 90°. The first inner structure 2a thereby forms a hollow cylindrical web-like structure.

As can be seen in FIGS. 5a to 5b the outer structure 2b similarly comprises four helices 2b1, 2b2, 2b3 and 2b4 which are also arranged coaxially to the longitudinal axis L and are rotated with respect to each other by 90°. The diameter $d_2$ of the helices of the outer structure is larger than the diameter $d_1$ of the helices of the inner structure but smaller than the outer diameter D of the rod-shaped implant 1. The outer structure 2b is rotated with respect to the inner structure 2a by 180°. The outer structure 2b also forms a hollow cylindrical net-like or web-like structure. As can be seen in FIGS. 6a, 6b and 1 to 3 the outer structure 2b encompasses the inner structure 2a in the rod-shaped implant.

The helices are made of fibers that have a high strength in the direction in which the fiber extends. The spring-like properties like the tensile strength and the compression strength of the fiber is defined by the geometry of the fibers. Hence, the distance and number of windings of the helices, the thickness of the fibers as well as the diameters $d_1$ and $d_2$ define the flexible characteristics of the helices and therefore of the whole flexible structure 2.

The material of the fibers is preferably a polymer such as polypropylene or a similar material. However, carbon or kevlar fibers may also be used. The material can be the same for the helices of the inner structure and the outer structure or can be different to provide specific properties. The difference between the elastic modulus of the fibers and that of the polymer matrix is less than between a metal spring and the polymer matrix. Therefore the risk of loosening of the fibers within the polymer matrix during load is small or does not exist.

The rod-shaped implant 1 is manufactured, for example, by first assembling the inner structure and the outer structure and then injection molding the polymer matrix around the whole flexible structure 2 so that the flexible structure 2 is embedded in the polymer matrix 3.

FIGS. 7 to 9 show the fixation of the rod-shaped implant in a monoaxial pedicle screw. The pedicle screw 5 includes a threaded shank 6 and a receiving part 7 formed at one end of the threaded shank 6. The receiving part 7 is substantially cylindrical and includes a U-shaped recess 8 extending from the free end in the direction of the threaded shank thereby forming two free legs on which an inner thread 9 is provided. At the bottom of the U-shaped recess an engagement structure 10 in the form of ribs extending transversely to the longitudinal axis L of the rod-shaped implant is provided. For fixation a fixation screw 11 is provided which can be screwed into the inner thread 9 of the receiving part 7. The fixation screw 11 includes an engagement structure 12 at its side facing the U-shaped implant 1 which can be, as shown in FIGS. 8 and 9, a ring-shaped projection.

In use at least two pedicle screws 5 are screwed in to adjacent vertebrae and the rod-shaped implant 1 is inserted and fixed by the fixation screw. The engagement structure 10 of the receiving part and the engagement structure 12 of the fixation screw press onto the rod-shaped implant 1, thereby deforming the surface of the polymer matrix 3 in such a way that a partially form-fit connection is generated between the engagement structure and the polymer matrix which holds the rod-shaped implant safe in place. The dimensions of the engagement structures are designed such that the flexible structure of the rod-shaped implant 1 is not deformed when tightening the fixation screw 11.

FIGS. 10 to 12 show the fixation of the rod-shaped implant in a polyaxial pedicle screw. The polyaxial pedicle screw 15 includes a screw member 16 with a threaded shank and a spherically-shaped head 16a and a receiving part 17. The receiving part 17 is substantially cylindrical and comprises a U-shaped recess 18 and a coaxial bore 19 which tapers into an opening 20 in which the head 16a of the screw member 16a is held so that it can pivot with respect to the receiving part 17. With the U-shaped recess 18 two free legs are formed having an inner thread 21. A pressure member 22 is provided by which pressure can be exerted onto the head 16a to fix the head 16a. The pressure member 22 can be inserted into the bore 19 and is designed to receive the rod-shaped implant 1. A fixation screw 23 is provided which comprises an engagement structure 24 at its side facing the rod-shaped implant 1.

In use, at least two pedicle screws are screwed into adjacent vertebrae, the receiving parts 17 are aligned to receive the rod-shaped implant which is then fixed by the fixation screw 23. By exerting pressure onto the pressure member 22 the head 16a is fixed in its position. Simultaneously the rod-shaped implant is fixed in the receiving part.

FIGS. 13 to 15 show the rod-shaped implant 1 fixed to two polyaxial pedicle screws 15, 15' anchored in the pedicles of adjacent vertebrae 101, 102 enclosing an intervertebral disk 103 between each other. FIG. 13 shows the neutral position. In this position the flexible structure 2 and the polymer matrix of the rod-shaped implant are neither compressed nor extended. FIG. 14 shows the condition of flexion of the spine wherein the distance of the pedicles and hence of the pedicle screws become larger than in the neutral position. The tensile force acting onto the rod-shaped implant causes the inner and the outer structures 2a, 2b to extend together with the surrounding polymer matrix. FIG. 15 shows the condition of extension of the spine where the pedicles approach each other so that the distance between the pedicle screws becomes smaller than in the neutral position. This compression force causes the inner structure and the outer structure to be compressed together with the polymer matrix so that the rod-shaped implant becomes shorter.

Figure 16:
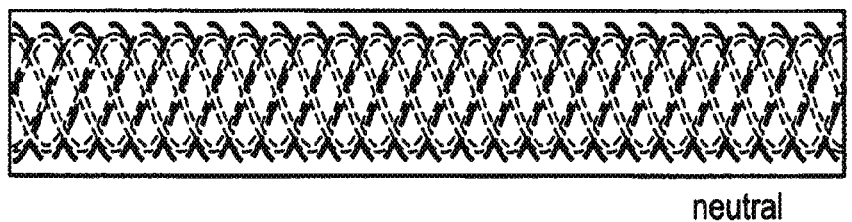
FIG. 16 shows a schematic side view of the rod-shaped implant in the neutral state.
Figure 17:
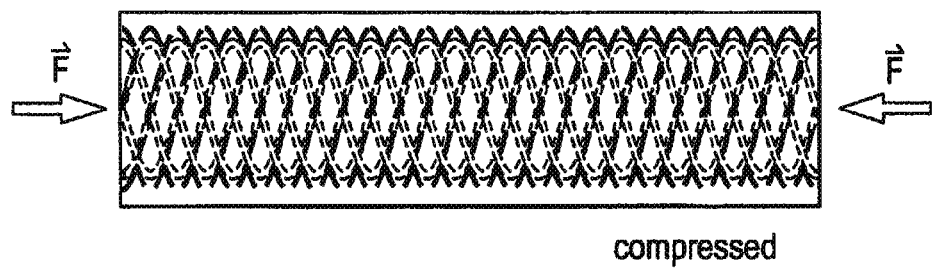
FIG. 17 shows a schematic side view of the rod-shaped implant under the action of an axial compression force.

FIG. 16 shows the length of the rod-shaped implant schematically in the neutral position and FIG. 14 shows the compression and shortening of the length of the rod-shaped implant. When the flexible structure is compressed by an axial force F the diameter of the inner structure and the outer structure becomes larger. Since the polymer matrix is an elastomer material it follows the compression or extension of the flexible structure 2.

Figure 18:
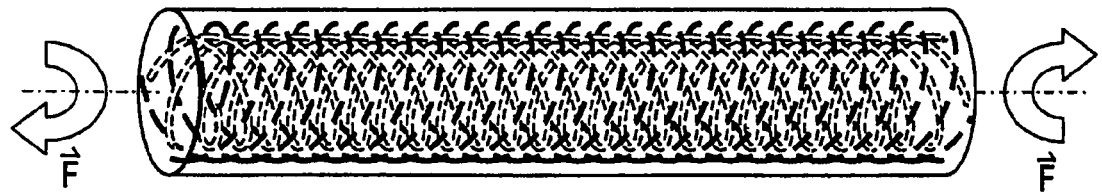
FIG. 18 shows the rod-shaped implant under the action of a torsional force.

When a torsional force F acts around the longitudinal axis of the rod-shaped implant as shown in FIG. 18 the flexible structure 2 withstands this torsional force so that a twisting of the rod-shaped implant is very small or practically does not occur. Since the inner structure and the outer structure are rotated against each other by 180° a high torsional stiffness can be provided. The torsional stiffness of the rod-shaped implant can be designed specifically by selecting the flexible properties of the flexible structure.

Due to the strength of the fibers, kinking of the rod-shaped implant is also very small or does not occur.

Figure 19A:
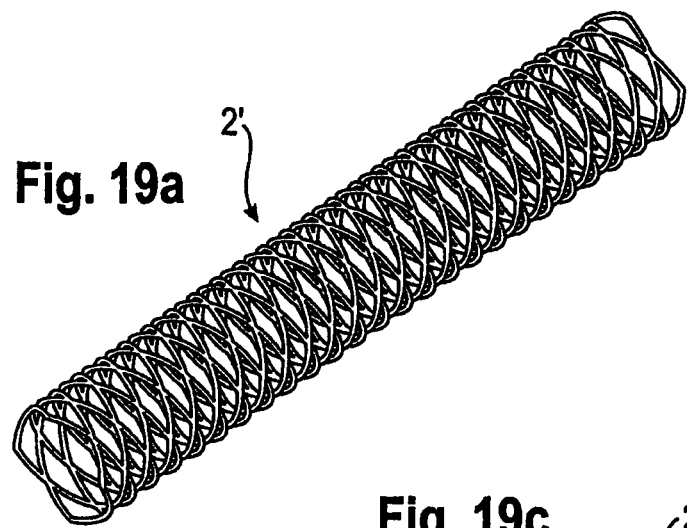
FIGS. 19a to 19c show a perspective view, a sectional view and a side view, respectively, of the flexible structure according to a modified embodiment.
Figure 19B:
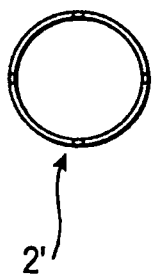
Figure 19C:
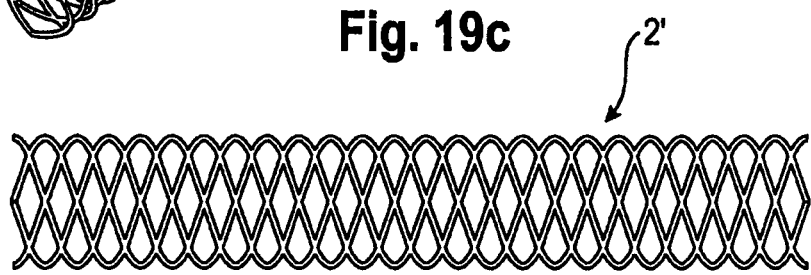

FIGS. 19a to 19c show a second embodiment of the flexible structure of the rod-shaped implant. It differs from the first embodiment shown in FIGS. 1 to 18 in that the outer structure has the same diameter than the inner structure. The inner and outer helices are connected in a net or web structure.

Figure 20A:
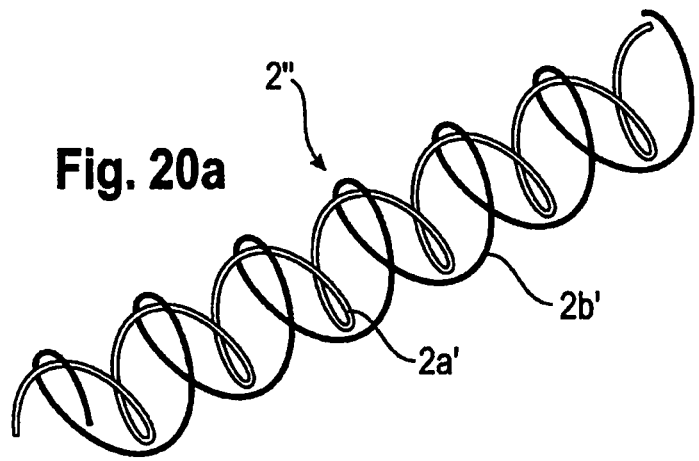
FIGS. 20a and 20b show a perspective view and a side view, respectively, of the flexible structure according to a further modified embodiment.
Figure 20B:
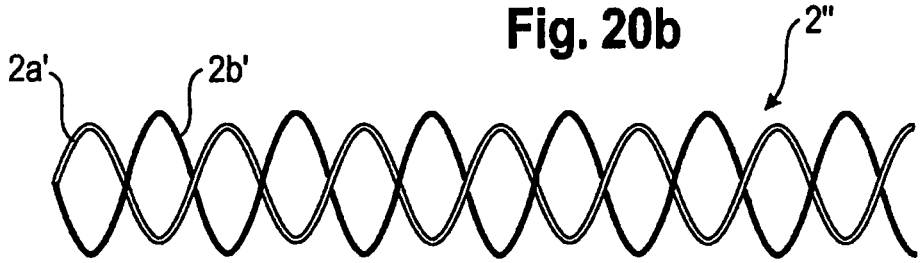

FIGS. 20a and 20b show a further modification of the flexible structure. The flexible structure consists on one single inner helix 2a' and one single outer helix 2b' having a larger diameter than that of the inner helix and being rotated by 180° with respect to the inner helix.

Further modifications are conceivable. The pitch of the windings of the helices can vary within one single helix or between different helices. The flexible structure does not necessarily have to be composed of helices. It can also be another net or web structure made of fibers, for example a fabric-like structure with diamond shaped openings or any other net or web structure which allows extension and compression while providing rotational stiffness.

Instead of the pedicle screws any other bone anchoring devices can be used.

While a particular form of the disclosure has been illustrated and described, it will be apparent that various modifications can be made without departing from the spirit and scope of the disclosure. Accordingly, it is not intended that the disclosure be limited, except as by the appended claims.

What is claimed is:

1. A rod-shaped implant for the dynamic stabilization of the spine, the rod-shaped implant comprising:
    a rod-shaped portion comprising a flexible first material forming a matrix; and
    a flexible structure embedded inside the matrix and comprising:
        two first fibers comprising a second material different from the first material and formed in first helical springs to increase torsional stiffness of the flexible structure in a first direction; and
        two second fibers comprising a third material different from the first material and formed in second helical springs to increase torsional stiffness of the flexible structure in a second direction different from the first direction;
        wherein outer diameters of each of the second helical springs is smaller than inner diameters of each of the first helical springs, and wherein each of the first fibers has two free ends and is entirely spaced apart from the other first fiber in the matrix, and each of the second fibers has two free ends and is entirely spaced apart from the other second fiber in the matrix.

2. The rod-shaped implant of claim 1, wherein the first material is a polymer.

3. The rod-shaped implant of claim 1, wherein the first material is an elastomeric material.

4. The rod-shaped implant of claim 1, wherein at least one of the second material and the third material is a synthetic material.

5. The rod-shaped implant of claim 1, wherein at least one of the second material and the third material is polypropylene.

6. The rod-shaped implant of claim 1, wherein the first helical springs are rotated against the second helical springs by an angle.

7. The rod-shaped implant of claim 6, wherein the angle is 180°.

8. The rod-shaped implant of claim 1, wherein the first helical springs have the same diameter.

9. The rod-shaped implant of claim 1, wherein the first helical springs have different diameters.

10. The rod-shaped implant of claim 1, wherein the second helical springs have the same diameter.

11. The rod-shaped implant of claim 1, wherein the second helical springs have different diameters.

12. The rod-shaped implant of claim 1, wherein the flexible structure defines a net-like structure configured to enhance torsional stiffness.

13. The rod-shaped implant of claim 1, wherein the second helical springs define an inner coaxial net-like structure and wherein the first helical springs define an outer coaxial net-like structure arranged around the inner structure.

14. The rod-shaped implant of claim 1, wherein the flexible structure comprises four first fibers configured in four first helical springs to define a net-like outer structure and four second fibers configured in four second helical springs to define a net-like inner structure.

15. The rod-shaped implant of claim 14, wherein the second helical springs of the inner structure are rotated against each other by 90° and the first helical springs of the outer structure are rotated against each other by 90°.

16. The rod-shaped implant of claim 14, wherein the inner structure and the outer structure are rotated against each other by 180°.

17. The rod-shaped implant of claim 1, wherein the flexible first material forming the matrix is cylindrical.

18. A bone anchoring assembly for dynamic stabilization of the spine comprising:
    a first bone anchoring element configured for attachment to a bone or vertebrae;
    a second bone anchoring element configured for attachment to a bone or vertebrae; and
    a rod-shaped implant configured to connect the first bone anchoring element to the second bone anchoring element, the rod-shaped implant comprising:
        a rod-shaped portion comprising a flexible first material forming a matrix; and
        a flexible structure embedded inside the matrix and comprising:
            two first fibers comprising a second material different from the first material and formed in first helical springs to increase torsional stiffness of the flexible structure in a first direction; and
            two second fibers comprising a third material different from the first material and formed in second helical springs to increase torsional stiffness of the flexible structure in a second direction different than the first direction;
            wherein outer diameters of each of the second helical springs is smaller than inner diameters of each of the first helical springs, and wherein each of the first fibers has two free ends and is entirely spaced apart from the other first fiber in the matrix, and each of the second fibers has two free ends and is entirely spaced apart from the other second fiber in the matrix.

19. A method of using a rod-shaped implant for dynamic stabilization of the spine with a first bone anchoring element configured for attachment to a bone or vertebrae, a second bone anchoring element configured for attachment to a bone or vertebrae, and a rod-shaped implant configured to connect the first bone anchoring element to the second bone anchoring element, the rod-shaped implant comprising a rod-shaped portion comprising a flexible first material forming a matrix, and a flexible structure embedded inside the matrix and comprising two first fibers comprising a second material different from the first material and formed in first helical springs to increase torsional stiffness of the flexible structure in a first direction, and two second fibers comprising a third material different from the first material and formed in second helical springs to increase torsional stiffness of the flexible structure in a second direction different than the first direction, wherein outer diameters of each of the second helical springs is smaller than inner diameters of each of the first helical springs, and wherein each of the first fibers has two free ends and is entirely spaced apart from the other first fiber in the matrix, and each of the second fibers has two free ends and is entirely spaced apart from the other second fiber in the matrix, the method comprising:

attaching the first bone anchoring element to a bone or vertebrae;

attaching the second bone anchoring element to a bone or vertebrae;

connecting the rod-shaped implant to the first bone anchoring element; and connecting the rod-shaped implant to the second bone anchoring element.

20. A rod-shaped implant for the dynamic stabilization of the spine, the rod-shaped implant comprising:

a rod-shaped portion comprising a flexible first material forming a matrix and defining a longitudinal axis; and a flexible monolithic net or web structure embedded inside the matrix and comprising:

at least a first helical portion made of a second material different from the first material and rotating in a first direction about the longitudinal axis; and at least a second helical portion made from the second material and rotating in a second direction about the longitudinal axis opposite from the first direction;

wherein the diameters of the first helical portion and the second helical portion are the same, and wherein a portion of the first helical portion located between ends of the first helical portion intersects a portion of the second helical portion located between ends of the second helical portion at an intersecting portion and the intersecting portion forms both a part of the first helical portion and the second helical portion intersect.

\* \* \* \* \*

UNITED STATES PATENT AND TRADEMARK OFFICE
CERTIFICATE OF CORRECTION

PATENT NO. : 9,072,545 B2
APPLICATION NO. : 12/435894
DATED : July 7, 2015
INVENTOR(S) : Lutz Biedermann et al.

It is certified that error appears in the above-identified patent and that said Letters Patent is hereby corrected as shown below:

In the Claims

Column 8, Claim 20, line 8      Delete "from"

Column 8, Claim 20, line 16      Delete "intersect"

Signed and Sealed this
Twenty-sixth Day of April, 2016

Michelle K. Lee
*Director of the United States Patent and Trademark Office*